United States Patent
Ahuja

(10) Patent No.: US 9,945,771 B2
(45) Date of Patent: Apr. 17, 2018

(54) MEASURING CRITICAL SHEAR STRESS FOR MUD FILTERCAKE REMOVAL

(71) Applicant: Halliburton Energy Services, Inc., Houston, TX (US)

(72) Inventor: Gopal Nevandram Ahuja, Pune (IN)

(73) Assignee: Halliburton Energy Services, Inc., Houston, TX (US)

( * ) Notice: Subject to any disclaimer, the term of this patent is extended or adjusted under 35 U.S.C. 154(b) by 92 days.

(21) Appl. No.: 15/030,002

(22) PCT Filed: Nov. 19, 2013

(86) PCT No.: PCT/US2013/070685
§ 371 (c)(1),
(2) Date: Apr. 15, 2016

(87) PCT Pub. No.: WO2015/076779
PCT Pub. Date: May 28, 2015

(65) Prior Publication Data
US 2016/0356697 A1 Dec. 8, 2016

(51) Int. Cl.
| | | |
|---|---|---|
| G01N 17/00 | (2006.01) |
| E21B 37/00 | (2006.01) |
| E21B 49/00 | (2006.01) |
| E21B 21/00 | (2006.01) |
| E21B 33/14 | (2006.01) |

(Continued)

(52) U.S. Cl.
CPC ......... *G01N 17/002* (2013.01); *E21B 21/003* (2013.01); *E21B 33/14* (2013.01); *E21B 37/00* (2013.01); *E21B 49/006* (2013.01); *G01N 3/567* (2013.01); *G01N 33/24* (2013.01)

(58) Field of Classification Search
CPC ........ E21B 21/003; E21B 33/14; E21B 37/00; E21B 49/006; G01N 17/002; G01N 33/24; G01N 3/567
See application file for complete search history.

(56) References Cited

U.S. PATENT DOCUMENTS

| | | | | |
|---|---|---|---|---|
| 4,185,706 A | * | 1/1980 | Baker, III | ................. E21B 7/18 175/340 |
| 4,474,251 A | * | 10/1984 | Johnson, Jr. | ............ B05B 17/06 175/67 |
| 4,829,816 A | | 5/1989 | Hubbard | |

(Continued)

OTHER PUBLICATIONS

Amanullah, Md. "A Novel Method of Assessment of Spurt and Filtrate Related Formation Damage Potential of Drilling and Drilling-in Fluids." SPE Asia Pacific Oil and Gas Conference and Exhibition. SPE 80484. Society of Petroleum Engineers, 2003.

(Continued)

*Primary Examiner* — Francis Gray
(74) *Attorney, Agent, or Firm* — John W. Wustenberg; Baker Botts L.L.P.

(57) ABSTRACT

Methods include: forming a first mud filtercake with a first mud; and determining a relationship between an impinging jet of a fluid at varying pressures against a surface of the first mud filtercake to a first erosion characteristic of the first mud filtercake. In various embodiments, the methods can additionally include: using the first erosion characteristic to design an operation to remove a second mud filtercake formed or to be formed in a wellbore with a second mud.

31 Claims, 2 Drawing Sheets

(51) Int. Cl.
  *G01N 3/56* (2006.01)
  *G01N 33/24* (2006.01)

(56) References Cited

U.S. PATENT DOCUMENTS

| | | | |
|---|---|---|---|
| 5,309,761 A | 5/1994 | Ravi et al. | |
| 5,484,016 A * | 1/1996 | Surjaatmadja | E21B 4/006 166/104 |
| 8,191,416 B2 * | 6/2012 | Kuchuk | E21B 49/008 73/152.41 |
| 2003/0029230 A1 | 2/2003 | Murphy, Jr. et al. | |
| 2004/0014606 A1 * | 1/2004 | Parlar | C09K 8/52 507/100 |
| 2009/0126940 A1 * | 5/2009 | Moen | E21B 37/08 166/376 |
| 2010/0126252 A1 * | 5/2010 | Bailey | G01N 11/14 73/54.28 |
| 2010/0126717 A1 * | 5/2010 | Kuchuk | E21B 49/008 166/250.03 |
| 2010/0139914 A1 | 6/2010 | Tehrani et al. | |

OTHER PUBLICATIONS

Extended Search Report issued in related EP Application No. 13897954.7, dated Apr. 19, 2017 (6 pages).
International Search Report and Written Opinion issued in related PCT Application No. PCT/US2013/070685 dated Aug. 21, 2014, 17 pages.
Vardy, S., et al. "Calibration of the high-pressure cohesive strength meter (CSM)." Continental Shelf Research 27.8 (2007): 1190-1199.
Widdows, J., et al. "Inter-comparison between five devices for determining erodability of intertidal sediments." Continental Shelf Research 27.8 (2007): 1174-1189.
Tolhurst, Travor J., Rolf Riethmüller, and David M. Paterson. "In situ versus laboratory analysis of sediment stability from intertidal mudflats." Continental Shelf Research 20.10 (2000): 1317-1334.
Paterson, D. M., et al. "Variation in sediment stability and sediment properties across the skeffling mudflat." Humber Estuary, UK Continental Shelf Research 20 (2000): 1373-1396.
Tolhurst, T. J., et al. "A comparison and measurement standardisation of four in situ devices for determining the erosion shear stress of intertidal sediments." Continental Shelf Research 20.10 (2000): 1397-1418.
Black, Kevin S., et al. "Incipient erosion of biostabilized sediments examined using particle-field optical holography." Environmental science & technology 35.11 (2001): 2275-2281.
Friend, Patrick L., and Carl L. Amos. "Natural coastal mechanisms—flume and field experiments on links between biology, sediments, and flow." Continental Shelf Research 27.8 (2007): 1017-1019.
McCave, I. N. "Sand waves in the North Sea off the coast of Holland." Marine geology 10.3 (1971): 199-225.
Simon, A., R. E. Thomas, and L. Klimetz. "Comparison and experiences with field techniques to measure critical shear stress and erodibility of cohesive deposits." 2nd Joint Federal Interagency Conference, Las Vegas, NV. 2010.
Tolhurst, T. J., et al. "Measuring the in situ erosion shear stress of intertidal sediments with the Cohesive Strength Meter (CSM)." Estuarine, Coastal and Shelf Science 49.2 (1999): 281-294.
Watts, C. W., et al. "In situ measurements of erosion shear stress and geotechnical shear strength of the intertidal sediments of the experimental managed realignment scheme at Tollesbury, Essex, UK." Estuarine, Coastal and Shelf Science 58.3 (2003): 611-620.
Bagnold, R. A. "An approach to the sediment transport problem." General Physics Geological Survey, Prof. paper (1966).
Tolhurst, T. J., et al. "The effects of rain on the erosion threshold of intertidal cohesive sediments." Aquatic Ecology 40.4 (2006): 533-541.
International Preliminary Report on Patentability issued in related Application No. PCT/US2013/070685, dated Jun. 2, 2016 (15 pages).

* cited by examiner

MEASURING CRITICAL SHEAR STRESS FOR MUD FILTERCAKE REMOVAL

CROSS-REFERENCE TO RELATED APPLICATION

The present application is a U.S. National Stage Application of International Application No. PCT/US2013/070685 filed Nov. 19, 2013, which is incorporated herein by reference in its entirety for all purposes.

TECHNICAL FIELD

The disclosure is in the field of producing crude oil or natural gas from subterranean formations. More specifically, the disclosure relates to methods for determining an erosion characteristic of a mud filtercake, such as a mud filtercake that may be formed in a wellbore during a drilling operation. Applications of the methods include without limitation, for example, the designing of operations for wellbore cleanout prior to cementing in a well.

GENERAL DISCLOSURE

Mud filtercake removal is a key issue to achieve successful zonal isolations. This provides a complete and durable seal along the well, effective bonding between casing, cement, and formation and provide for minimum slurry contamination. Ineffective mud removal will not only affect well completion jobs and testing, but may also lead to formation communication and severe production losses as well as secondary cementing jobs.

Mud filtercake cleaning from the borehole wall by cleaning systems requires a good understanding of the fundamental phenomenon associated with the erosional behavior of mud filtercakes formed by different mud systems. Because of serious consequences of mud filtercake erosion on the formation damage potential of drilling muds and mud filtercake cleaning before a cementation job, it is important to have a suitable and simple method for determining or predicting the erosional potential of mud filtercakes formed by muds of different compositions.

A purpose of this disclosure is to provide apparatuses and methods for determining an erosion characteristic, such as the critical horizontal shear stress ($\tau_0$) required at the walls of a well bore to remove drilling fluid deposits, such as a mud filtercake. Knowledge of the critical horizontal shear stress ($\tau_0$) required allows the drilling fluid to be circulated at a proper rate to efficiently remove the drilling fluid deposits, or for special spacer fluid or other means to be employed to bring about such removal prior to placing primary cement slurry in the well bore.

According to the disclosure, methods are provided that include the steps of: forming a first mud filtercake with a first mud; and determining a relationship between an impinging jet of a fluid at varying pressures against a surface of the first mud filtercake to a first erosion characteristic of the first mud filtercake.

In various embodiments, the methods can additionally include the step of: using the first erosion characteristic to design an operation to remove a second mud filtercake formed or to be formed in a wellbore with a second mud.

In various embodiments, methods according to this disclosure can be used to assess the effectiveness of mud filtercake cleaning operations and to help design such cleaning operations for removal of mud filtercake from a borehole in a well.

In various embodiments, methods according to the disclosure can be used for designing fluids such as drilling fluids, spacer fluids, or for designing the conditions of introducing such well fluids into a well for the removal of a mud filtercake in the well.

These and other aspects of the disclosure will be apparent to one skilled in the art upon reading the following detailed description. While the disclosure is susceptible to various modifications and alternative forms, specific embodiments thereof will be described in detail and shown by way of example. It should be understood, however, that it is not intended to limit the disclosure to the particular forms disclosed, but, on the contrary, the disclosure is to cover all modifications and alternatives falling within the spirit and scope of the disclosure as expressed in the appended claims.

BRIEF DESCRIPTION OF THE DRAWING

The accompanying drawing is incorporated into the specification to help illustrate examples according to the presently most-preferred embodiment of the disclosure.

DETAILED DESCRIPTION OF PRESENTLY PREFERRED EMBODIMENTS AND BEST MODE

Well Servicing and Well Fluids

Figure 1:
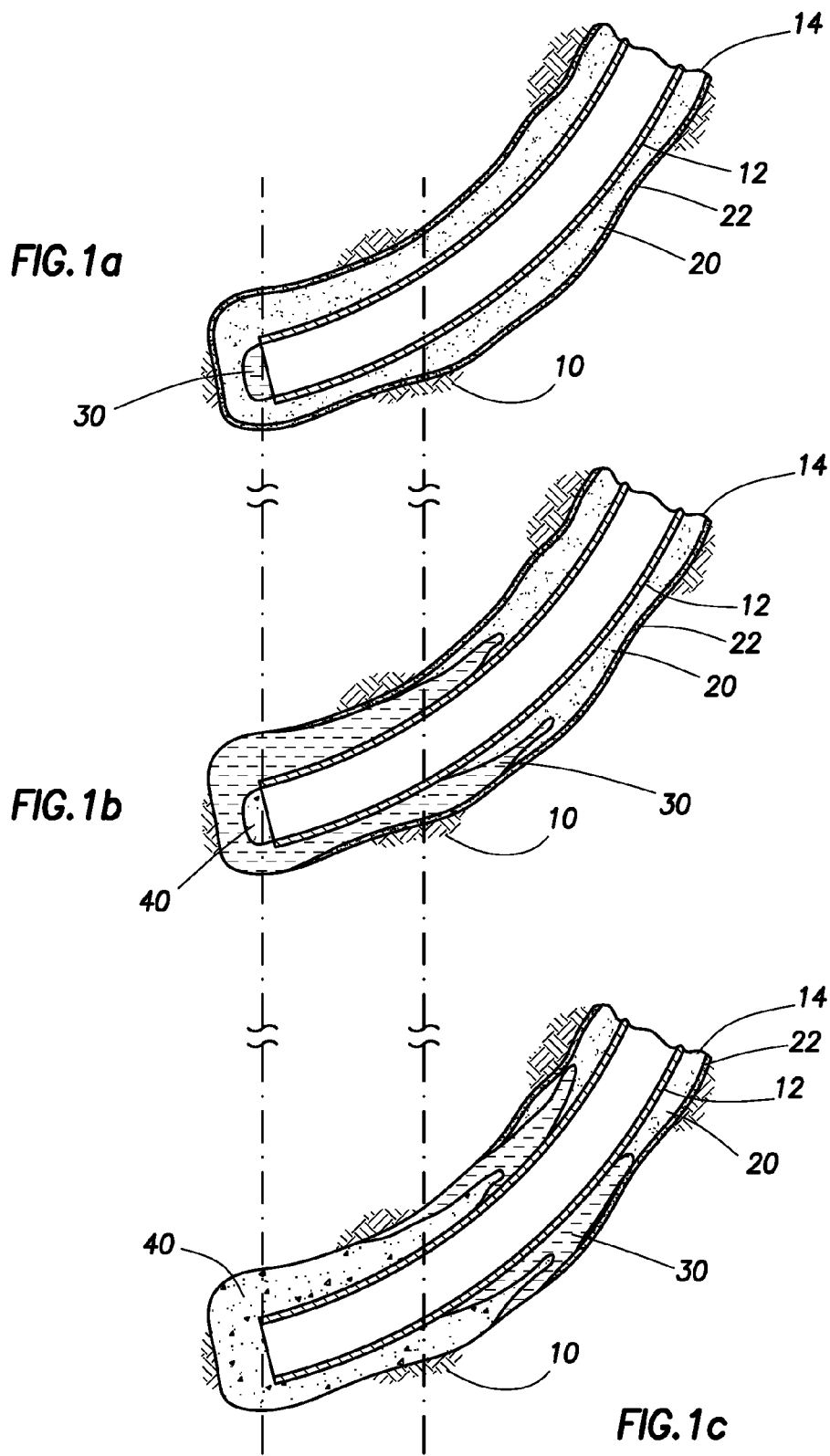
FIGS. 1a, 1b, and 1c are illustrations of a sequence of fluid displacement in a wellbore during a cementing operation.

To produce oil or gas, a well is drilled into a subterranean formation that is an oil or gas reservoir.

Generally, well services include a wide variety of operations that may be performed in oil, gas, geothermal, or water wells, such as drilling, cementing, completion, and intervention. Well services are designed to facilitate or enhance the production of desirable fluids, such as oil or gas, from or through a subterranean formation. A well service usually involves introducing a fluid into a well.

Drilling is the process of drilling the wellbore. After a portion of the wellbore is drilled, sections of steel pipe, referred to as casing, which are slightly smaller in diameter than the borehole, are placed in at least the uppermost portions of the wellbore. The casing provides structural integrity to the newly drilled borehole.

Cementing is a common well operation. For example, hydraulic cement compositions can be used in cementing operations in which a string of pipe, such as casing or liner, is cemented in a wellbore. The cement stabilizes the pipe in the wellbore and prevents undesirable migration of fluids along the annulus between the wellbore and the outside of the casing or liner from one zone along the wellbore to the next. Where the wellbore penetrates into a hydrocarbon-bearing zone of a subterranean formation, the casing can later be perforated to allow fluid communication between the zone and the wellbore. The cemented casing also enables subsequent or remedial separation or isolation of one or more production zones of the wellbore, for example, by using downhole tools such as packers or plugs, or by using other techniques, such as forming sand plugs or placing cement in the perforations. Hydraulic cement compositions can also be utilized in intervention operations, such as in plugging highly permeable zones or fractures in zones that may be producing too much water, plugging cracks or holes in pipe strings, and the like.

Completion is the process of making a well ready for production or injection. This principally involves preparing a zone of the wellbore to the required specifications, running in the production tubing and associated downhole equipment, as well as perforating and stimulating as required.

Intervention is any operation carried out on a well during or at the end of its productive life that alters the state of the well or well geometry, provides well diagnostics, or manages the production of the well. Workover can broadly refer to any kind of well intervention that involves invasive techniques, such as wireline, coiled tubing, or snubbing. More specifically, however, workover usually refers to a process of pulling and replacing a completion.

Drilling

The well is created by drilling a hole into the earth (or seabed) with a drilling rig that rotates a drill string with a drilling bit attached to the downward end. Usually the borehole is anywhere between about 5 inches (13 cm) to about 36 inches (91 cm) in diameter. As upper portions are cased or lined, progressively smaller drilling strings and bits must be used to pass through the uphole casings or liners, which steps the borehole down to progressively smaller diameters.

While drilling an oil or gas well, a drilling fluid is circulated downhole through a drillpipe to a drill bit at the downhole end, out through the drill bit into the wellbore, and then back uphole to the surface through the annular path between the tubular drillpipe and the borehole. The purpose of the drilling fluid is to maintain hydrostatic pressure in the wellbore, lubricate the drill string, and carry rock cuttings out from the wellbore.

The drilling fluid can be water-based or oil-based. Oil-based fluids tend to have better lubricating properties than water-based fluids, nevertheless, other factors can mitigate in favor of using a water-based drilling fluid. Such factors may include but not limited to presence of water-swellable formations, need for a thin but a strong and impermeable filtercake, temperature stability, corrosion resistance, stuck pipe prevention, contamination resistance and production protection.

Fluid-Loss Control and Filtercake Formation

Fluid loss refers to the undesirable leakage of a fluid phase of any type of drilling or treatment fluid into the permeable matrix of a subterranean formation. Fluids used in drilling, completion, or servicing of a wellbore can be lost to a subterranean formation while circulating the fluids in the wellbore. In particular, the fluids may enter the subterranean formation via depleted zones, zones of relatively low pressure, lost circulation zones having naturally occurring fractures, weak zones having fracture gradients exceeded by the hydrostatic pressure of the drilling fluid, and so forth. The extent of fluid losses to the formation may range from minor (for example less than 10 bbl/hr), which is referred to as seepage loss, to severe (for example, greater than 500 bbl/hr), which is referred to as complete loss. The greater the fluid loss, the more difficult it is to achieve the purpose of the fluid.

Fluid-loss control refers to treatments designed to reduce fluid loss. Providing effective fluid-loss control for fluids during certain stages of well operations is usually highly desirable.

Fluid-loss control fluids typically include an aqueous continuous phase and a high concentration of a viscosifying agent (usually crosslinked), and usually, bridging particles, such as graded sand, graded salt particulate, or graded calcium carbonate particulate. Through a combination of viscosity, solids bridging, and cake buildup on the porous rock of the borehole, such fluids are often able to substantially reduce the permeability of a zone of the subterranean formation to fluid loss.

For example, commonly-used fluid-loss control pills contain high concentrations (100 to 150 lb/1000 gal) of derivatized hydroxyethylcellulose ("HEC"). HEC is generally accepted as a viscosifying agent affording minimal permeability damage during completion operations. Normally, HEC polymer solutions do not form rigid gels, but control fluid loss by a viscosity-regulated or filtration mechanism. Some other viscosifying polymers that have been used include xanthan, guar, guar derivatives, carboxymethylhydroxyethylcellulose ("CMHEC"), and starch. Viscoelastic surfactants can also be used.

Crosslinked polymers can also be used for fluid-loss control. Crosslinking the gelling agent polymer helps suspend solids in a fluid as well as provide fluid-loss control. Further, crosslinked fluid-loss control pills have demonstrated that they require relatively limited invasion of the formation face to be fully effective. To crosslink the viscosifying polymers, a suitable crosslinking agent that includes polyvalent metal ions is used. Boron, aluminum, titanium, and zirconium are common examples.

A preferred crosslinkable viscosifying polymer for fluid-loss control pills are graft copolymers of a hydroxyalkyl cellulose, guar, or hydroxypropyl guar that are prepared by a redox reaction with vinyl phosphonic acid. Crosslinks can be formed by hydrating the graft copolymer in an aqueous solution containing at least a trace amount of at least one divalent cation. The addition of a Lewis base or Bronsted-Lowrey adjusts the pH of the aqueous solution from slightly acidic to slightly basic. Preferably, the chosen base is substantially free of polyvalent metal ions. The resulting crosslinked gel demonstrates shear-thinning and rehealing properties that provide relatively easy pumping, while the rehealed gel provides good fluid-loss control upon placement. Some fluid-loss pills of this type are described in U.S. Pat. No. 5,304,620, assigned to Halliburton Energy Services. Fluid-loss control pills of this type are commercially available under the trade name "K-MAX" from Halliburton Energy Services Inc. in Duncan, Okla.

The usual approach to fluid-loss control is to substantially reduce the permeability of the matrix of the zone with a fluid-loss control material that blocks the permeability at or near the face of the rock matrix of the zone. For example, the fluid-loss control material may be a particulate that has a size selected to bridge and plug the pore throats of the matrix. As the fluid phase carrying the fluid-loss control material leaks into the formation, the fluid-loss control material bridges the pore throats of the matrix of the formation and builds up on the surface of the borehole or fracture face or penetrates only a little into the matrix. All else being equal, the higher the concentration of the appropriately sized particulate, the faster bridging will occur.

The buildup of solid particulate or other fluid-loss control material on the walls of a wellbore or a fracture is referred to as a filtercake. Such a filtercake can help block the further loss of a fluid phase (referred to as a filtrate) into the subterranean formation. A fluid-loss control material is specifically designed to lower the volume of a filtrate that passes through a filter medium. Accordingly, a fluid-loss control material is sometimes referred to as a filtration control agent.

Examples of fluid-loss control agents include, but are not limited to, starches, silica flour, gas bubbles (energized fluid or foam), benzoic acid, soaps, resin particulates, relative permeability modifiers, degradable particulates, diesel dispersed in fluid, and other immiscible fluids.

A fluid-loss control agent can be included in a drilling or treatment fluid in a concentration necessary to give the desired fluid-loss control. In some embodiments, a fluid-loss additive may be included in a concentration of about 5 to about 200 lb/Mgal of the treatment fluid. In some embodiments, the fluid-loss additive may be included in a concentration from about 10 to about 50 lb/Mgal of the treatment fluid.

For some liquid fluid-loss control agents, such as diesel, these may be included in a concentration from about 0.01% to about 20% by volume of the treatment fluid; in some embodiments, these may be included in a concentration from about 1% to about 10% by volume of the treatment fluid.

Filtercake Clean-Up

After application of a mud filtercake, the mud cake must be removed so a cement can form an effective seal with the borehole of a formation.

A filtercake can be removed, for example, by erosion, dissolving the bridging particulate, chemically degrading the viscosity-increasing agent, reversing or breaking crosslinking if the viscosity-increasing agent is crosslinked, or a combination of these. More particularly, for example, a fluid-loss control agent can be selected for being insoluble in water but soluble in acid, whereby changing the pH or washing with an acidic fluid can dissolve the fluid-loss control agent. Chemically degrading the viscosity-increasing agent, reversing or breaking crosslinking if the viscosity-increasing agent is crosslinked, can be another technique for removing a filtercake.

Cementing and Hydraulic Cement Compositions

Hydraulic cement is a material that when mixed with water hardens or sets over time because of a chemical reaction with the water. The cement composition sets by a hydration process, passing through a gel phase to solid phase. Because this is a chemical reaction with water, hydraulic cement is capable of setting even under water.

The hydraulic cement, water, and any other components are mixed to form a hydraulic cement composition in fluid form. The hydraulic cement composition is pumped as a fluid (typically in the form of suspension or slurry) into a desired location in the wellbore. For example, in cementing a casing or liner, the hydraulic cement composition is pumped into the annular space between the exterior surfaces of a pipe string and the borehole (that is, the wall of the wellbore). The hydraulic cement composition should be a fluid for a sufficient time before setting to allow for pumping the composition into the wellbore and for placement in a desired downhole location in the well. The cement composition is allowed time to set in the annular space, thereby forming an annular sheath of hardened, substantially impermeable cement. The hardened cement supports and positions the pipe string in the wellbore and fills the annular space between the exterior surfaces of the pipe string and the borehole of the wellbore.

DEFINITIONS AND USAGES

General Interpretation

The words or terms used herein have their plain, ordinary meaning in the field of this disclosure, except to the extent explicitly and clearly defined in this disclosure or unless the specific context otherwise requires a different meaning.

If there is any conflict in the usages of a word or term in this disclosure and one or more patent(s) or other documents that may be incorporated by reference, the definitions that are consistent with this specification should be adopted.

The words "comprising," "containing," "including," "having," and all grammatical variations thereof are intended to have an open, non-limiting meaning. For example, a composition comprising a component does not exclude it from having additional components, an apparatus comprising a part does not exclude it from having additional parts, and a method having a step does not exclude it having additional steps. When such terms are used, the compositions, apparatuses, and methods that "consist essentially of" or "consist of" the specified components, parts, and steps are specifically included and disclosed. As used herein, the words "consisting essentially of," and all grammatical variations thereof are intended to limit the scope of a claim to the specified materials or steps and those that do not materially affect the basic and novel characteristic(s) of the claimed invention.

The indefinite articles "a" or "an" mean one or more than one of the component, part, or step that the article introduces.

Each numerical value should be read once as modified by the term "about" (unless already expressly so modified), and then read again as not so modified, unless otherwise indicated in context.

Whenever a numerical range of degree or measurement with a lower limit and an upper limit is disclosed, any number and any range falling within the range is also intended to be specifically disclosed. For example, every range of values (in the form "from a to b," or "from about a to about b," or "from about a to b," "from approximately a to b," and any similar expressions, where "a" and "b" represent numerical values of degree or measurement) is to be understood to set forth every number and range encompassed within the broader range of values.

It should be understood that algebraic variables and other scientific symbols used herein are selected arbitrarily or according to convention. Other algebraic variables can be used.

Terms such as "first," "second," "third," etc. may be assigned arbitrarily and are merely intended to differentiate between two or more components, parts, or steps that are otherwise similar or corresponding in nature, structure, function, or action. For example, the words "first" and "second" serve no other purpose and are not part of the name or description of the following name or descriptive terms. The mere use of the term "first" does not require that there be any "second" similar or corresponding component, part, or step. Similarly, the mere use of the word "second" does not require that there be any "first" or "third" similar or corresponding component, part, or step. Further, it is to be understood that the mere use of the term "first" does not require that the element or step be the very first in any sequence, but merely that it is at least one of the elements or steps. Similarly, the mere use of the terms "first" and "second" does not necessarily require any sequence. Accordingly, the mere use of such terms does not exclude intervening elements or steps between the "first" and "second" elements or steps, etc.

The control or controlling of a condition includes any one or more of maintaining, applying, or varying of the condition. For example, controlling the temperature of a substance can include heating, cooling, or thermally insulating the substance.

Well Terms

In the context of production from a well, oil and gas are understood to refer to crude oil and natural gas. Oil and gas are naturally occurring hydrocarbons in certain subterranean formations.

A "subterranean formation" is a body of rock that has sufficiently distinctive characteristics and is sufficiently continuous for geologists to describe, map, and name it.

A subterranean formation having a sufficient porosity and permeability to store and transmit fluids is sometimes referred to as a "reservoir."

A subterranean formation containing oil or gas may be located under land or under the seabed off shore. Oil and gas reservoirs are typically located in the range of a few hundred feet (shallow reservoirs) to a few tens of thousands of feet (ultra-deep reservoirs) below the surface of the land or seabed.

A "well" includes a wellhead and at least one wellbore from the wellhead penetrating the earth. The "wellhead" is the surface termination of a wellbore, which surface may be on land or on a seabed.

A "well site" is the geographical location of a wellhead of a well. It may include related facilities, such as a tank battery, separators, compressor stations, heating or other equipment, and fluid pits. If offshore, a well site can include a platform.

The "wellbore" refers to the drilled hole, including any cased or uncased portions of the well or any other tubulars in the well. The "borehole" usually refers to the inside wellbore wall, that is, the rock surface or wall that bounds the drilled hole. A wellbore can have portions that are vertical, horizontal, or anything in between, and it can have portions that are straight, curved, or branched. As used herein, "uphole," "downhole," and similar terms are relative to the direction of the wellhead, regardless of whether a wellbore portion is vertical or horizontal.

A wellbore can be used as a production or injection wellbore. A production wellbore is used to produce hydrocarbons from the reservoir. An injection wellbore is used to inject a fluid, e.g., liquid water or steam, to drive oil or gas to a production wellbore.

As used herein, introducing "into a well" means introduced at least into and through the wellhead. According to various techniques known in the art, tubulars, equipment, tools, or well fluids can be directed from the wellhead into any desired portion of the wellbore.

As used herein, the word "tubular" means any kind of structural body in the general form of a tube. Tubulars can be of any suitable body material, but in the oilfield they are most commonly of steel. Examples of tubulars in oil wells include, but are not limited to, a drill pipe, a casing, a tubing string, a liner pipe, and a transportation pipe.

As used herein, the term "annulus" means the space between two generally cylindrical objects, one inside the other. The objects can be concentric or eccentric. Without limitation, one of the objects can be a tubular and the other object can be an enclosed conduit. The enclosed conduit can be a wellbore or borehole or it can be another tubular. The following are some non-limiting examples illustrating some situations in which an annulus can exist. Referring to an oil, gas, or water well, in an open hole well, the space between the outside of a tubing string and the borehole of the wellbore is an annulus. In a cased hole, the space between the outside of the casing and the borehole is an annulus. In addition, in a cased hole there may be an annulus between the outside cylindrical portion of a tubular, such as a production tubing string, and the inside cylindrical portion of the casing. An annulus can be a space through which a fluid can flow or it can be filled with a material or object that blocks fluid flow, such as a packing element. Unless otherwise clear from the context, as used herein an "annulus" is a space through which a fluid can flow.

A fluid can be, for example, a drilling fluid, a setting composition, a treatment fluid, or a spacer fluid. If a fluid is to be used in a relatively small volume, for example less than about 200 barrels (about 8,400 US gallons or about 32 $m^3$), it is sometimes referred to as a wash, dump, slug, or pill.

Drilling fluid means the circulating fluid (mud) used in the rotary drilling of wells to clean and condition the hole and to counterbalance formation pressure. Drilling fluids, also known as drilling muds or simply "muds," are typically classified according to their base fluid (that is, the continuous phase). Classes of drilling fluids include: (1) Water-based drilling fluid means the continuous phase and suspending medium for solids is a water-miscible fluid, regardless of the presence of oil. (2) Non-aqueous drilling fluid means the continuous phase and suspending medium for solids is a water-immiscible fluid, such as oleaginous materials (for example, mineral oil, enhanced mineral oil, paraffinic oil, C16-C18 internal olefins, and C8-C16 fatty acid/2-ethylhexyl esters). Oil-based means the continuous phase of the drilling fluid consists of diesel oil, mineral oil, or some other oil, but contains no synthetic material or enhanced mineral oil. Enhanced mineral oil-based means the continuous phase of the drilling fluid is enhanced mineral oil. Synthetic-based means the continuous phase of the drilling fluid is a synthetic material or a combination of synthetic materials.

A water-based mud ("WBM") typically has solid particulate (e.g., clays, bulk density increasing agents, lost circulation materials,) suspended in an aqueous liquid as the continuous phase. The water can be brine. A brine-based drilling fluid is a water-based mud in which the aqueous component is brine. In some cases, oil may be emulsified in a water-based drilling mud.

An oil-based mud ("OBM") has solid particulate suspended in oil as the continuous phase. In some cases, an aqueous phase of water or brine is emulsified in the oil.

As the drilling process begins and continues, drill cuttings from the formation will be suspended as additional solid particulates in an oil-based or water-based mud.

As used herein, the word "treatment" refers to any treatment for changing a condition of any portion of a wellbore or an adjacent subterranean formation; however, the word "treatment" does not necessarily imply any particular treatment purpose. A treatment usually involves introducing a well fluid for the treatment, in which case it may be referred to as a treatment fluid, into a well. As used herein, a "treatment fluid" is a fluid used in a treatment. The word "treatment" in the term "treatment fluid" does not necessarily imply any particular treatment or action by the fluid.

As used herein, the terms spacer fluid, wash fluid, and inverter fluid can be used interchangeably. A spacer fluid is a fluid used to physically separate one special-purpose fluid from another. It may be undesirable for one special-purpose fluid to mix with another used in the well, so a spacer fluid compatible with each is used between the two. A spacer fluid is usually used when changing between well fluids used in a well.

For example, a spacer fluid is used to change from a drilling fluid during drilling to cement composition during cementing operations in the well. In case of an oil-based drilling fluid, it should be kept separate from a water-based cementing fluid. In changing to the latter fluid, a chemically treated water-based spacer fluid is usually used to separate the drilling fluid from the water-based cementing fluid.

Volumes of spacer fluid that are consumed in channel lengths due to contamination process are not sufficient to clean wellbore surfaces or change wetting of a surface. These volumes should be considered sacrificial and the amount of pure uncontaminated spacer is estimated from surface wetting techniques.

A "zone" refers to an interval of rock along a wellbore that is differentiated from uphole and downhole zones based on hydrocarbon content or other features, such as permeability, composition, perforations or other fluid communication with the wellbore, faults, or fractures. A zone of a wellbore that penetrates a hydrocarbon-bearing zone that is capable of producing hydrocarbon is referred to as a "production zone." A "treatment zone" refers to a zone into which a fluid is directed to flow from the wellbore. As used herein, "into a treatment zone" means into and through the wellhead and, additionally, through the wellbore and into the treatment zone.

Generally, the greater the depth of the formation, the higher the static temperature and pressure of the formation. Initially, the static pressure equals the initial pressure in the formation before production.

A "design" refers to the estimate or measure of one or more parameters planned or expected for a particular stage of a well service or associated well fluid. A well service may include design parameters such as fluid volume to be pumped, required pumping time for a treatment, or the shear conditions of the pumping, and contact time of a treatment fluid with a zone of interest.

The term "design temperature" refers to an estimate or measurement of the actual temperature at the downhole environment at the time of a well treatment. That is, design temperature takes into account not only the bottom hole static temperature ("BHST"), but also the effect of the temperature of the well fluid on the BHST during treatment. The design temperature is sometimes referred to as the bottom hole circulation temperature ("BHCT"). Because treatment fluids may be considerably cooler than BHST, the difference between the two temperatures can be quite large. Ultimately, if left undisturbed, a subterranean formation will return to the BHST.

Physical States, Phases, and Materials

As used herein, "phase" is used to refer to a substance having a chemical composition and physical state that is distinguishable from an adjacent phase of a substance having a different chemical composition or a different physical state.

The word "material" is often used as a synonym for a single phase of a bulk scale (larger than a particle), although it can sometimes mean a bulk scale of a mixture of phases, depending on the context.

As used herein, if not other otherwise specifically stated, the physical state or phase of a substance (or mixture of substances) and other physical properties are determined at a temperature of 77° F. (25° C.) and a pressure of 1 atmosphere (Standard Laboratory Conditions) without applied shear.

Particles and Particulates

As used herein, a "particle" refers to a body having a finite mass and sufficient cohesion such that it can be considered as an entity but having relatively small dimensions. A particle can be of any size ranging from molecular scale to macroscopic, depending on context.

A particle can be in any physical state. For example, a particle of a substance in a solid state can be as small as a few molecules on the scale of nanometers up to a large particle on the scale of a few millimeters, such as large grains of sand. Similarly, a particle of a substance in a liquid state can be as small as a few molecules on the scale of nanometers or a large drop on the scale of a few millimeters.

As used herein, "particulate" or "particulate material" refers to matter in the physical form of distinct particles in a solid or liquid state (which means such an association of a few atoms or molecules). A particulate is a grouping of particles based on common characteristics, including chemical composition and particle size range, particle size distribution, or median particle size. As used herein, a particulate is a grouping of particles having similar chemical composition and particle size ranges anywhere in the range of about 1 micrometer (e.g., microscopic clay or silt particles) to about 3 millimeters (e.g., large grains of sand).

As used herein, a particle can be an aggregate or a composite of different solid phases bound together.

It should be understood that the terms "particle" and "particulate," includes all known shapes of particles including substantially rounded, spherical, oblong, ellipsoid, rod-like, fiber, polyhedral (such as cubic materials), etc., and mixtures thereof. For example, the term "particulate" as used herein is intended to include solid particles having the physical shape of platelets, shavings, flakes, ribbons, rods, strips, spheroids, toroids, pellets, tablets or any other physical shape.

A particulate will have a particle size distribution ("PSD"). As used herein, "the size" of a particulate can be determined by methods known to persons skilled in the art.

One way to define the particle size distribution is to cite distribution values such as the (0.10), d(0.50), or d(0.90). The d(0.50), which is sometimes referred to as the "D50" or the median particle size, is defined as the diameter where half of the particles are smaller and half are larger than the size. Similarly, 10 percent of the distribution lies below the d(0.10) or "D10" size, and 90 percent of the distribution lies below the d(0.90) or "D90" size.

One way to measure the approximate particle size distribution of a solid particulate is with graded screens. A solid particulate material will pass through some specific mesh (that is, have a maximum size; larger pieces will not fit through this mesh) but will be retained by some specific tighter mesh (that is, a minimum size; pieces smaller than this will pass through the mesh). This type of description establishes a range of particle sizes. A "+" before the mesh size indicates the particles are retained by the sieve, while a "−" before the mesh size indicates the particles pass through the sieve. For example, −70/+140 means that 90% or more of the particles will have mesh sizes between the two values.

The most commonly-used grade scale for classifying the diameters of sediments in geology is the Udden-Wentworth scale. According to this scale, a solid particulate having particles smaller than 2 mm in diameter is classified as sand, silt, or clay. Sand is a detrital grain between 2 mm (equivalent to 2,000 micrometers) and 0.0625 mm (equivalent to 62.5 micrometers) in diameter. (Sand is also a term sometimes used to refer to quartz grains or for sandstone.) Silt refers to particulate between 74 micrometers (equivalent to about −200 U.S. Standard mesh) and about 2 micrometers. Clay is a particulate smaller than 0.0039 mm (equivalent to 3.9 μm).

Dispersions

A dispersion is a system in which particles of a substance of one chemical composition and physical state are dispersed in another substance of a different chemical composition or physical state. If a substance has more than one phase, the most external phase is referred to as the continuous phase of the substance as a whole, regardless of the number of different internal phases or nested phases.

A dispersion can be classified a number of different ways, including based on the size of the dispersed particles, the uniformity or lack of uniformity of the dispersion, and, if a fluid, whether or not precipitation occurs.

A dispersion is considered to be heterogeneous if the dispersed particles are not dissolved and are greater than about 1 nanometer in size. (For reference, the diameter of a molecule of toluene is about 1 nm). Heterogeneous dispersions can have gas, liquid, or solid as an external phase. For example, in a case where the dispersed-phase particles are liquid in an external phase that is another liquid, this kind of heterogeneous dispersion is more particularly referred to as an emulsion. A solid dispersed phase in a continuous liquid phase is referred to as a sol, suspension, or slurry, partly depending on the size of the dispersed solid particulate.

A dispersion is considered to be homogeneous if the dispersed particles are dissolved in solution or the particles are less than about 1 nanometer in size. Even if not dissolved, a dispersion is considered to be homogeneous if the dispersed particles are less than about 1 nanometer in size.

Fluids

A fluid can be a single phase or a dispersion. In general, a fluid is an amorphous substance that is or has a continuous phase of particles that are smaller than about 1 micrometer that tends to flow and to conform to the outline of its container.

Examples of fluids are gases and liquids. A gas (in the sense of a physical state) refers to an amorphous substance that has a high tendency to disperse (at the molecular level) and a relatively high compressibility. A liquid refers to an amorphous substance that has little tendency to disperse (at the molecular level) and relatively high incompressibility. The tendency to disperse is related to Intermolecular Forces (also known as van der Waal's Forces).

As used herein, a fluid is a substance that behaves as a fluid under Standard Laboratory Conditions, that is, at 77° F. (25° C.) temperature and 1 atmosphere pressure, and at the higher temperatures and pressures usually occurring in subterranean formations without applied shear.

Every fluid inherently has at least a continuous phase. A fluid can have more than one phase. The continuous phase of a well fluid is a liquid under Standard Laboratory Conditions. For example, a well fluid can in the form of be a suspension (solid particles dispersed in a liquid phase), an emulsion (liquid particles dispersed in another liquid phase), or a foam (a gas phase dispersed in liquid phase).

As used herein, a water-based fluid means that water or an aqueous solution is the dominant material of the continuous phase, that is, greater than 50% by weight, of the continuous phase of the substance.

In contrast, "oil-based" means that oil is the dominant material by weight of the continuous phase of the substance. In this context, the oil of an oil-based fluid can be any oil. In general, an oil is any substance that is liquid Standard Laboratory Conditions, is hydrophobic, and soluble in organic solvents. Oils have a high carbon and hydrogen content and are relatively non-polar substances, for example, having a dielectric constant of 1.5 to 5. This general definition includes classes such as petrochemical oils, vegetable oils, and many organic solvents. All oils can be traced back to organic sources.

Cement Compositions

As used herein, "cement" refers to an inorganic cement (as opposed to organic cement and adhesives) that when mixed with water will begin to set and harden.

As used herein, a "cement composition" is a material including at least cement. A cement composition can also include additives. A cement composition can include water or be mixed with water.

A cement can be characterized as non-hydraulic or hydraulic.

Non-hydraulic cements (e.g., gypsum plaster, Sorel cements) must be kept dry in order to retain their strength.

Hydraulic cements (e.g., Portland cement) harden because of hydration, chemical reactions that occur independently of the mixture's water content; they can harden even underwater or when constantly exposed to wet weather. The chemical reaction that results when the dry cement powder is mixed with water produces hydrates that have extremely low solubility in water. The cement composition sets by a hydration process, and it passes through a gel phase to solid phase.

During well completion, it is common to introduce a cement composition into an annulus in the wellbore. For example, in a cased hole, the cement composition is placed into and allowed to set in the annulus between the wellbore and the casing in order to stabilize and secure the casing in the wellbore. After setting, the set cement composition should have a low permeability. Consequently, oil or gas can be produced in a controlled manner by directing the flow of oil or gas through the casing and into the wellhead. Cement compositions can also be used, for example, in well-plugging operations or gravel-packing operations.

Methods According to the Disclosure

FIGS. 1a, 1b, and 1c are illustrations of a sequence of fluid displacement in a wellbore during a cementing operation. A spacer fluid 30 is illustrated being pumped into a wellbore of a well penetrating a formation 10 and down through a casing 12 (which has not yet been cemented) and then out the lower end of the casing and up through the annulus 14 between the outside of the casing 12 and the borehole of the wellbore. FIG. 1a illustrates a drilling mud 20 initially the annulus 14 of the wellbore around the casing 12. FIG. 1b illustrates a spacer fluid 30 being pumped through the casing to displace the drilling mud 20 from the annulus 14. FIG. 1c illustrates a cement composition 40 (sometimes referred to as a cement slurry) being pumped through the casing 12 to displace the spacer fluid 30 and placed in the annulus 14 for cementing the casing 12 in the wellbore penetrating the formation 10. To seal the annulus 14 with cement requires good cement bonding between both the outer wall of the casing 12 and the rock of the subterranean formation 10 of the borehole.

In addition to merely displacing the drilling mud 20, it is also important to remove a mud filtercake 22 formed by the drilling mud 20 on the borehole of the wellbore.

According to the disclosure, methods are provided that include the steps of: forming a first mud filtercake with a first mud; and determining a relationship between an impinging jet of a fluid at varying pressures against a surface of the first mud filtercake to a first erosion characteristic of the first mud filtercake.

In various embodiments, the methods can additionally include the step of: using the first erosion characteristic to design an operation to remove a second mud filtercake formed or to be formed with a second mud in a wellbore.

Forming the First Mud Filtercake

In various embodiments, the first mud filtercake is formed outside of the wellbore. For example, the first mud filtercake can be formed on a filter, such as a glass frit or a filter paper.

First Mud Similar to or Same as Second Mud

In various embodiments, the first mud has a density that is within about 10% of the density of the second mud. Preferably and in various embodiments, the first mud has a density that is within about 5% of the density of the second mud.

In various embodiments, the first mud has similar composition to the second mud. For example, the first mud filtercake can have similar particulates as the second mud filtercake. As used herein, "similar" means such as would be comparable by a person of skill in the art for expecting the erosion characteristic of a mud filtercake formed with the first mud to be within about 10% of the erosion characteristic of a mud filtercake formed with the second mud. Preferably, the similarity is such that the erosion characteristic of a first mud filtercake formed by a first mud would be expected to be within about 5% of the erosion characteristic of a second mud filtercake formed by a second mud.

For example, the first mud can have similar or the same types and sizes clay or other particulates as the second mud. In addition, other components in a mud can affect an erosion characteristic of a mud filtercake formed with the mud. In various embodiments, the first mud is the same as the second mud.

First Mud Filtercake Similar to Second Mud Filtercake

In various embodiments, the first mud filtercake has similar particulates as the second mud. For example, the first mud filtercake can have similar or the same types and sizes clay or other particulates as the second mud filtercake. In addition, other components in a mud can affect an erosion characteristic of a mud filtercake formed with the mud.

In various embodiments, the first mud filtercake is formed under similar filtration conditions to the second mud filtercake. For example, the permeability and differential pressure across a filter material, such as filter media can be within about 10% of the permeability and differential pressure across the borehole in a treatment zone of a formation.

Determining First Erosion Characteristic

In various embodiments, the impinging jet is in a test chamber containing the first mud filtercake or having a wall portion thereof defined by the first mud filtercake. Preferably, the test chamber includes the fluid of the impinging fluid covering the surface of the first mud filtercake without shear except for the impinging jet of the fluid. The impinging jet of the fluid can then displace the fluid in the test chamber.

In various embodiments, the impinging jet of the fluid is perpendicular to the surface of the first mud filtercake. For example, the impinging jet of the fluid can be vertical and the surface of the first mud filtercake can be horizontal.

In various embodiments, the fluid of the impinging jet has a continuous liquid phase. For example, the fluid of the impinging jet can comprise water.

In various embodiments, the fluid of the impinging jet is transmissive of at least one wavelength of ultraviolet light, visible light, or infrared light. A substance in the first mud filtercake should be opaque to the at least one wavelength. The test chamber can have a light source of the at least one wavelength and a light sensor of the at least one wavelength that are operatively positioned to measure the light transmissiveness of the fluid in the test chamber. The impinging jet of the fluid at varying pressures can be related to observing a reduction in light transmissiveness of the fluid in the test chamber due to erosion of the surface of the first mud filtercake.

In various embodiments, a reduction in light transmissiveness of the fluid in the test chamber at one of the varying pressures of the impinging jet of the fluid is used to determine the relationship between the impinging jet of the fluid at varying pressures against the surface of the first mud filtercake to an erosion characteristic of the first mud filtercake. For example, the impinging jet pressure at which a reduction in light transmissiveness is observed can be related to a critical horizontal shear stress required for erosion of the first mud filtercake. In various embodiments, the critical horizontal shear stress required for erosion of the first mud filtercake is related to a horizontal rate of flow for a fluid having a known density. For example, the reduction in light transmissiveness of the fluid in the test chamber to 90% of the light transmissiveness of the fluid of the impinging jet can be considered to indicate incipient motion of particles of the first mud filtercake.

Using the First Erosion Characteristic to Design a Removal Operation

In various embodiments, using the first erosion characteristic can include considering the first erosion characteristic to be similar to a second erosion characteristic of the second filtercake. For example, using the first erosion characteristic can include considering the first erosion characteristic to be within about 10% of a second erosion characteristic of the second filtercake. In some embodiments, using the first erosion characteristic can include considering the first erosion characteristic to be within about 5% of a second erosion characteristic of the second filtercake. In another example, using the first erosion characteristic can include considering the first erosion characteristic to be about the same as a second erosion characteristic of the second filtercake.

Forming Second Filtercake in the Wellbore

In various embodiments, the methods can additionally include the step of: forming the second mud filtercake in the wellbore.

Using the Operation for Removal of Filtercake from the Wellbore

In various embodiments, the methods can additionally include the step of: using the operation to remove the second mud filtercake from the wellbore. For example, the operation can include applying a horizontal shear stress across a surface of the second mud filtercake formed by the second mud used or to be used in the wellbore. The horizontal shear stress can be at least the critical horizontal shear stress as determined according to an embodiment of the disclosed methods.

Applications

In various embodiments, the methods according to the disclosure can be used for the determination or prediction of an erosion characteristic of a mud filtercake, such as a critical horizontal shear stress ($\tau_c$) or a shear velocity of a liquid across the surface of a mud filtercake. This can be used to help design operations for the removal of different types of mud filtercakes formed by various different types of drilling fluids.

In various embodiments, the methods according to the disclosure can be used to provide a correlation between an operational factor such as shear velocity of a liquid across the surface of a mud filtercake to an erosion rate of the filtercake.

In various embodiments, the methods according to the disclosure can be used to assess the effectiveness of a mud filtercake cleaning operation and to help design such mud filtercake cleaning operations for removal of mud filtercake from the borehole of a well.

In various embodiments, the methods according to the disclosure, an erosion characteristic, such as a critical horizontal shear stress ($\tau_c$), can be used to determine that a fluid should be circulated at a sufficient rate to efficiently remove the drilling fluid deposits.

In various embodiments, the methods according to the disclosure, can be used for the erosion characterization of a mud filtercake formed from a mud of a certain type of composition.

In various embodiments, the methods can be used to help select a mud design or additives that will produce a mud filtercake having a sufficiently low erosion characteristic for effective removal of the mud filtercake from a borehole. The mud additives can be tested and selected, for example, to reduce the adhesion or sticking properties of the deposited mud filtercake so that it has lower affinity to stick to drill pipe, drill bit, and bottom-hole assembly ("BHA"), or a lower affinity to bind the impregnated cuttings to the mud filtercake matrix In various embodiments of the methods according to the disclosure, they can help with an appropriate selection of a spacer or wash fluid for a given drilling mud and filtercake.

In various embodiments, values of an erosion characteristic, such as ($\tau_c$), can be used for the correct prediction of the contact time between the spacer or wash fluid and the mud filtercake to achieve the appropriate mud filtercake removal.

Example Test Apparatus

Figure 2:
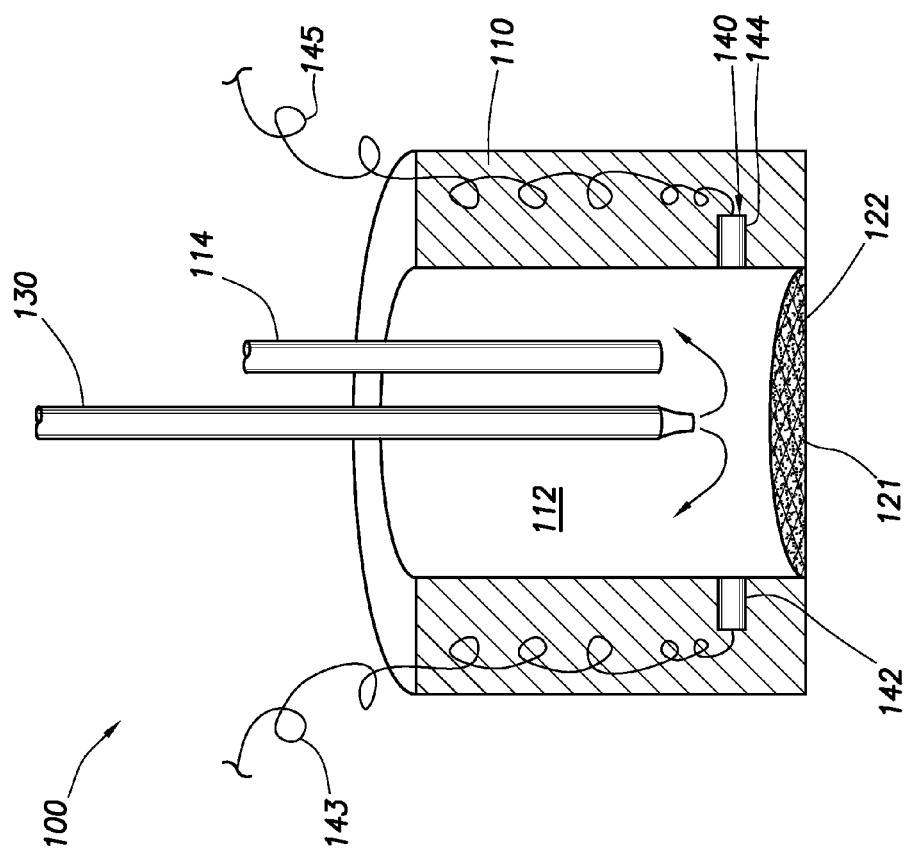
FIG. 2 is a cross-sectional schematic illustration of an example of a test apparatus that can be used according to the methods of this disclosure.

FIG. 2 is a schematic representation of an example of a test apparatus 100 for testing an erosion characteristic of a mud filtercake, such as may be formed in a drilling operation to create or extend a wellbore of a well.

The test apparatus 100 is based upon the principle of a vertical jet of water impinging at varying pressures on a horizontal surface of a mud filtercake formed in the apparatus. The apparatus can permit rapid assessment of an erosion characteristic, such as the critical horizontal shear stress of the mud filtercake.

The test apparatus 100 includes a chamber wall 110 at least partially defining or forming a chamber 112. A fill tube 114 can be provided, which can be used for filling the chamber 112 with a fluid, such as a first mud for forming a filtercake, or displacing the remaining mud after forming a filtercake with a test fluid.

A first mud filtercake 122 can be formed with a first mud (not shown) in the test apparatus 100. For example, the first mud filtercake 120 can define or form a bottom wall portion defining or forming the chamber 112. The first mud filtercake can be formed, for example, by introducing a first mud into the chamber and allowing or causing a pressure differential across a filter material, such as a glass frit or a filter paper 121, to form the filtercake 122.

A jet tube 130 is oriented in the test apparatus 100 toward a surface of the filtercake 122. A jet of fluid can be directed through the jet tube 130 to impinge on the surface of the filtercake 122 formed in the test apparatus 100. The jet tube 130 can have, for example, a 1 mm internal diameter. The jet of fluid through the jet tube 130 can be driven, for example, by pressure source, such as a tank of pressurized air, a source of the fluid, and a pneumatic or hydraulic pipe system with appropriate controls, which can be computer controlled, as will be appreciated by those of skill in the art of such equipment. The jet of fluid and varying pressures exiting the jet tube 130 and impinging against the filtercake 122 can be controlled, for example, with a computer and associated electronics, as will be appreciated by those of skill in the art of such equipment.

The test apparatus includes a transmissiveness detector 140. The transmissiveness detector can include a light emitter 142 and a light sensor 144 positioned in the apparatus 110 to detect light transmissiveness of a fluid in the chamber 112. The light emitter 142 can be, for example, an emitter of at least one wavelength of ultraviolet light, visible light, or infrared light. The light sensor 144 is selected to detect and measure the at least one wavelength of light from the light emitter 142. The light emitter can be, for example, a light emitting diode ("LED"). A suitable electrical cable 143 is operatively connected to the light emitter 142 and a suitable electrical cable 145 is operatively connected to the light sensor 144. The electrical cable 145 can include communication regarding information from the light sensor 144. The at least one wavelength of light can be, for example, a wavelength of infrared light. The transmissiveness detector 140 can be connected to a computer (not shown) for controlling the apparatus 100.

The fill tube 114 can be used to allow excess fluid from the jet of fluid to overflow from the chamber 112.

The test apparatus 100 can include a computer (not shown) or be connected to a computer for controlling the various functions of the test apparatus, for example, the forming of a mud filtercake 122 in the apparatus, varying the pressure of a jet of fluid impinging on a surface of the mud filtercake 122, logging the light transmissiveness of a fluid in the chamber 112 during the testing, correlating the pressure of jet of fluid to a light transmissiveness of a fluid in the chamber to determine an erosion characteristic of the mud filtercake, and reporting the results.

The test apparatus 100 can be on a small scale, for example, it can be on laboratory bench scale and used in a laboratory remote from a well site or in a test facility at or near a well site. Optionally, for example, the equipment can be battery powered.

An example of such an apparatus that can be use or adapted for use according to the methods of this disclosure is disclosed, for example, in T. J. Tolhurst, K. S. Black, S. A. Shayler, S. Mather, I. Black, K. Baker, and D. M. Paterson, Measuring the in situ Erosion Shear Stress of Intermedial Sediments with the Cohesive Strength Meter (CSM), Estuarine Coastal and Shelf Science (1999) 49, 281-294. The Cohesive Strength Meter (CSM) is a compact, portable field instrument which directly measures a surface erodibility characteristic of sediment surfaces. CSM is a well-tested instrument for use in measuring environmental erosion, for example, in water streams or soil), which has been used to provide erosion threshold data on both cohesive and non-cohesive sediments for various soil erosion studies. According to an embodiment of this disclosure, such an instrument can be adapted to measure an erosion characteristic of a mud filtercake, which information can be used in designing an operation to remove a second mud filtercake formed or to be formed in a wellbore with a second mud.

Example Determination of Erosion Characteristic

A test apparatus 100 can be used to determine an erosion characteristic. For example, the apparatus 100 employs a stress induced by the jet of fluid to erode the mud filtercake 120 in the chamber 112. Jet pressure is increased in increments while the light transmission in the chamber 112 is recorded. A reduction in transmission is associated with an increase in sediment suspension associated with erosion of the mud filtercake 120.

For example, the fluid used in the jet of fluid preferably has a transmissiveness to the at least one wavelength of light that is nearly 100%. As the stress induced by the jet of fluid increases, the mud filtercake 120 begins to erode. The particulates that are eroded from the mud filtercake are dispersed into the fluid in the chamber 112. As the solid particulates block light transmissiveness through the fluid, increasing erosion will be indicated by a reduction in the light transmissiveness of the fluid in the chamber 112.

The reducing in light transmissiveness can be correlated to the stress induced by the jet of fluid, as will be appreciated by persons in the field. For example, the shear stress corresponding to a reduction in light transmission to 90% of the starting transmissiveness value can be considered to indicate incipient motion of particles and thus represents a critical shear stress ($\tau_c$) of the material being tested. Andrew Simon, Robert E. Thomas, Lauren Klimetz, Comparison and Experiences with Field Techniques to Measure Critical Shear Stress and Erodibility of Cohesive Deposits, 2nd Joint Federal Interagency Conference, Las Vegas, Nev., Jun. 27-Jul. 1, 2010.

The pressure step when this drop occurs is taken as the critical eroding pressure (kPa) which can be converted to an equivalent horizontal shear stress $\tau_c$ (N/m$^2$) using an empirical relationship or calibration of a particular type of such erosion test equipment. Such a determination can be accomplished according to techniques for measuring erosion in other fields. For example, an empirical calibration based on the equation of Bagnold (1966), modified by McCave (1971) permits the expression of the eroding jet pressure in terms of equivalent horizontal shear stress (N/m$^2$) for the equipment used in T. J. Tolhurst, K. S. Black, S. A. Shayler, S. Mather, I. Black, K. Baker, and D. M. Paterson, Measuring the in situ Erosion Shear Stress of Intermedial Sediments with the Cohesive Strength Meter (CSM), Estuarine Coastal and Shelf Science (1999) 49, 281-294. As reported in this literature, this relationship is given by the relationship of Equation 1:

$$\tau_c = y_0 + A1 \times [1 - \exp(-x/t1)] + A2 \times [1 - \exp(-x/t2)] \quad \text{(Equation 1)}$$

where:
$\tau_c$=horizontal shear stress (N m$^{-2}$);
$y_o$=zero;
x=eroding pressure (kPa);
A1=a constant (67);
A2=a constant (−195);
t1=a constant (310); and
t2=a constant (1623).

T. J. Tolhurst, K. S. Black, S. A. Shayler, S. Mather, I. Black, K. Baker, and D. M. Paterson, Measuring the in situ Erosion Shear Stress of Intermedial Sediments with the Cohesive Strength Meter (CSM), Estuarine Coastal and Shelf Science (1999) 49, 281-294.

The critical horizontal shear stress can be converted to shear velocity (U*) across a surface of the mud filtercake by the following relationship of Equation 2:

$$U^* = (\tau_c/\rho)^{0.5} \quad \text{(Equation 2)}$$

where:
U*=shear velocity (m s$^{-1}$);
$\rho$=density of shearing fluid, e.g., water, 1,000 (kg m$^{-3}$); and
$\tau_c$=horizontal shear stress, N m$^{-2}$.

See, T. J. Tolhurst, K. S. Black, S. A. Shayler, S. Mather, I. Black, K. Baker, and D. M. Paterson, Measuring the in situ Erosion Shear Stress of Intermedial Sediments with the Cohesive Strength Meter (CSM), Estuarine Coastal and Shelf Science (1999) 49, 281-294.

As will be appreciated by a person skilled in such fields, such a relationships is empirically determined, and the relationship may depend on the exact structure of the apparatus employed.

CONCLUSION

Therefore, the present disclosure is well adapted to attain the ends and advantages mentioned as well as those that are inherent therein.

The exemplary fluids disclosed herein may directly or indirectly affect one or more components or pieces of equipment associated with the preparation, delivery, recapture, recycling, reuse, or disposal of the disclosed fluids. For example, the disclosed fluids may directly or indirectly affect one or more mixers, related mixing equipment, mud pits, storage facilities or units, fluid separators, heat exchangers, sensors, gauges, pumps, compressors, and the like used generate, store, monitor, regulate, or recondition the exemplary fluids. The disclosed fluids may also directly or indirectly affect any transport or delivery equipment used to convey the fluids to a well site or downhole such as, for example, any transport vessels, conduits, pipelines, trucks, tubulars, or pipes used to fluidically move the fluids from one location to another, any pumps, compressors, or motors (for example, topside or downhole) used to drive the fluids into motion, any valves or related joints used to regulate the pressure or flow rate of the fluids, and any sensors (i.e., pressure and temperature), gauges, or combinations thereof, and the like. The disclosed fluids may also directly or indirectly affect the various downhole equipment and tools that may come into contact with the chemicals/fluids such as, but not limited to, drill string, coiled tubing, drill pipe, drill collars, mud motors, downhole motors or pumps, floats, MWD/LWD tools and related telemetry equipment, drill bits (including roller cone, PDC, natural diamond, hole openers, reamers, and coring bits), sensors or distributed sensors, downhole heat exchangers, valves and corresponding actuation devices, tool seals, packers and other wellbore isolation devices or components, and the like.

The particular embodiments disclosed above are illustrative only, as the present disclosure may be modified and practiced in different but equivalent manners apparent to those skilled in the art having the benefit of the teachings herein. It is, therefore, evident that the particular illustrative embodiments disclosed above may be altered or modified and all such variations are considered within the scope of the present disclosure.

The various elements or steps according to the disclosed elements or steps can be combined advantageously or practiced together in various combinations or sub-combinations of elements or sequences of steps to increase the efficiency and benefits that can be obtained from the disclosure.

It will be appreciated that one or more of the above embodiments may be combined with one or more of the other embodiments, unless explicitly stated otherwise.

The illustrative disclosure can be practiced in the absence of any element or step that is not specifically disclosed or claimed.

Furthermore, no limitations are intended to the details of construction, composition, design, or steps herein shown, other than as described in the claims.

What is claimed is:

1. A method comprising:
   forming a first mud filtercake with a first mud; and
   determining a relationship between an impinging jet of a fluid at varying pressures against a surface of the first mud filtercake to a first erosion characteristic of the first mud filtercake, wherein the impinging jet is in a test chamber containing the first mud filtercake or having a wall portion thereof defined by the first mud filtercake.

2. The method according to claim 1, additionally comprising:
   using the first erosion characteristic to design an operation to remove a second mud filtercake formed or to be formed in a wellbore with a second mud.

3. The method according to claim 2, wherein the first mud filtercake is formed outside of the wellbore.

4. The method according to claim 2, wherein the first mud filtercake is formed on a filter.

5. The method according to claim 2, wherein the first mud has a density that is within about 10% of the density of the second mud.

6. The method according to claim 2, wherein the first mud has similar composition to the second mud.

7. The method according to claim 2, wherein the first mud filtercake has similar particulates as the second mud filtercake.

8. The method according to claim 2, wherein the first mud is the same composition as the second mud.

9. The method according to claim 2, wherein the first mud filtercake has similar particulates as the second mud filtercake.

10. The method according to claim 2, wherein the first mud filtercake is formed under similar filtration conditions to the second mud filtercake.

11. The method according to claim 1, wherein the test chamber includes the fluid of the impinging fluid covering the surface of the first mud filtercake without shear except for the impinging jet of the fluid.

12. The method according to claim 11, wherein the impinging jet of the fluid displaces the fluid in the test chamber.

13. The method according to claim 12, wherein the impinging jet of the fluid is perpendicular to the surface of the first mud filtercake.

14. The method according to claim 13, wherein the impinging jet of the fluid is vertical and the surface of the first mud filtercake is horizontal.

15. The method according to claim 13, wherein the impinging jet of the fluid is downward.

16. The method according to claim 12, wherein the fluid of the impinging jet has a continuous liquid phase.

17. The method according to claim 16, wherein the fluid of the impinging jet comprises water.

18. The method according to claim 12, wherein the fluid of the impinging jet is transmissive of at least one wavelength of ultraviolet light, visible light, or infrared light.

19. The method according to claim 10, wherein a substance in the first mud filtercake is opaque to the at least one wavelength.

20. The method according to claim 19, wherein the test chamber has a light source of the at least one wavelength and a light sensor of the at least one wavelength that are operatively positioned to measure the light transmissiveness of the fluid in the test chamber.

21. The method according to claim 20, wherein the impinging jet of the fluid at varying pressures can be related to a reduction in light transmissiveness of the fluid in the test chamber due to erosion of the surface of the first mud filtercake.

22. The method according to claim 21, wherein a reduction in light transmissiveness of the fluid in the test chamber at one of the varying pressures of the impinging jet of the fluid is used to determine the relationship between the impinging jet of the fluid at varying pressures against the surface of the first mud filtercake to erosion of the first mud filtercake.

23. The method according to claim 22, wherein the impinging jet pressure at which a reduction in light transmissiveness is related to a critical horizontal shear stress required for erosion of the first mud filtercake.

24. The method according to claim 23, wherein the critical horizontal shear stress required for erosion of the first mud filtercake is related to a horizontal rate of flow for a fluid having a known density.

25. The method according to claim 21, wherein the reduction in light transmissiveness of the fluid in the test chamber to 90% of the light transmissiveness of the fluid of the impinging jet is considered to indicate incipient motion of particles of the first mud filtercake.

26. The method according to claim 2, wherein using the first erosion characteristic includes considering the first erosion characteristic to be similar to a second erosion characteristic of the second mud filtercake.

27. The method according to claim 2, wherein using the first erosion characteristic includes considering the first erosion characteristic to be within about 10% of a second erosion characteristic of the second mud filtercake.

28. The method according to claim 2, wherein using the first erosion characteristic includes considering the first erosion characteristic to be about the same as a second erosion characteristic of the second mud filtercake.

29. The method according to claim 2, additionally comprising:
    forming the second mud filtercake in the wellbore.

30. The method according to claim 2, additionally comprising: using the operation to remove the second mud filtercake from the wellbore.

31. The method according to claim 2, wherein the operation includes applying a horizontal shear stress across a surface of the second mud filtercake formed by the second mud used or to be used in the wellbore.

* * * * *